(12) United States Patent
Akao

(10) Patent No.: US 11,031,801 B2
(45) Date of Patent: Jun. 8, 2021

(54) POWER SUPPLY UNIT FOR AEROSOL INHALER

(71) Applicant: JAPAN TOBACCO INC., Tokyo (JP)

(72) Inventor: Takeshi Akao, Tokyo (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/745,038

(22) Filed: Jan. 16, 2020

(65) Prior Publication Data
US 2020/0229502 A1    Jul. 23, 2020

Related U.S. Application Data

(60) Provisional application No. 62/793,551, filed on Jan. 17, 2019.

(30) Foreign Application Priority Data

Feb. 28, 2019    (JP) .............................. JP2019-035984

(51) Int. Cl.
*A24F 40/90*    (2020.01)
*H02J 7/00*    (2006.01)
(Continued)

(52) U.S. Cl.
CPC ............ *H02J 7/0068* (2013.01); *A24F 40/40* (2020.01); *A24F 40/50* (2020.01); *A24F 40/51* (2020.01);
(Continued)

(58) Field of Classification Search
CPC .......... A24F 40/90; A24F 40/30; A24F 40/60; A24F 40/50; A24F 40/51; H02J 7/0068; H02J 7/0045; A61M 15/06
(Continued)

(56) References Cited

U.S. PATENT DOCUMENTS 8,678,012 B2 * 3/2014 Li et al. ................ A24F 47/008
131/270
8,948,578 B2 * 2/2015 Buchberger ......... A61M 11/042
392/395
(Continued)

FOREIGN PATENT DOCUMENTS

CN    103783674 A    5/2014
CN    206595747 U    10/2017
(Continued)

OTHER PUBLICATIONS

European Search Report issued in related European Patent Application No. 20152146.5 dated May 13, 2020.
(Continued)

*Primary Examiner* — Sun J Lin
(74) *Attorney, Agent, or Firm* — Venable LLP

(57) ABSTRACT

A power supply unit for an aerosol inhaler includes: a power supply able to discharge a power to a load for generating an aerosol from an aerosol source; a connector able to be electrically connected to an external power supply; and a control device. The power supply unit further includes: a conductor which electrically connects the connector and the control device; a capacitor provided between the connector and the control device so as to be connected in parallel with the control device; a first circuit board on which the connector is provided; a second circuit board which is apart from the first circuit board and on which the capacitor and the control device are provided; and a conductive member which electrically connects the first circuit board and the second circuit board.

12 Claims, 12 Drawing Sheets

(51) Int. Cl.

| | |
|---|---|
| A24F 40/50 | (2020.01) |
| A24F 40/60 | (2020.01) |
| A24F 40/51 | (2020.01) |
| A61M 15/06 | (2006.01) |
| A61M 15/00 | (2006.01) |
| H05K 1/18 | (2006.01) |
| A24F 40/53 | (2020.01) |
| H05K 1/14 | (2006.01) |
| A24F 40/40 | (2020.01) |
| G05F 3/18 | (2006.01) |
| H01M 10/42 | (2006.01) |
| A24F 40/95 | (2020.01) |
| H02J 7/04 | (2006.01) |
| A24F 40/30 | (2020.01) |

(52) U.S. Cl.
CPC .............. *A24F 40/53* (2020.01); *A24F 40/60* (2020.01); *A24F 40/90* (2020.01); *A24F 40/95* (2020.01); *A61M 15/009* (2013.01); *G05F 3/18* (2013.01); *H01M 10/425* (2013.01); *H02J 7/005* (2020.01); *H02J 7/007* (2013.01); *H02J 7/0042* (2013.01); *H02J 7/0045* (2013.01); *H02J 7/0063* (2013.01); *H02J 7/007194* (2020.01); *H02J 7/04* (2013.01); *H05K 1/14* (2013.01); *H05K 1/181* (2013.01); *A24F 40/30* (2020.01); *A61M 15/0003* (2014.02); *A61M 15/06* (2013.01); *A61M 2205/3653* (2013.01); *A61M 2205/50* (2013.01); *A61M 2205/8206* (2013.01); *A61M 2205/8237* (2013.01); *A61M 2205/8243* (2013.01); *H05K 2201/10015* (2013.01); *H05K 2201/10022* (2013.01); *H05K 2201/10174* (2013.01)

(58) Field of Classification Search
USPC ........................................................ 131/329
See application file for complete search history.

(56) References Cited

U.S. PATENT DOCUMENTS

| | | |
|---|---|---|
| 2012/0230659 A1 | 9/2012 | Goodman et al. |
| 2013/0199528 A1 | 8/2013 | Goodman et al. |
| 2014/0041658 A1 | 2/2014 | Goodman et al. |
| 2015/0020831 A1 | 1/2015 | Weigensberg et al. |
| 2015/0173124 A1 | 6/2015 | Qiu |
| 2016/0316822 A1 | 11/2016 | Liu |
| 2016/0331915 A1 | 11/2016 | Goodman et al. |
| 2016/0374397 A1 | 12/2016 | Jordan et al. |
| 2017/0094998 A1 | 4/2017 | Bernauer et al. |
| 2017/0208865 A1 | 7/2017 | Nettenstrom et al. |
| 2018/0015242 A1 | 1/2018 | Goodman et al. |
| 2018/0020728 A1 | 1/2018 | Alarcon et al. |
| 2018/0070635 A1 | 3/2018 | Litten |
| 2019/0380395 A1 | 12/2019 | Takeuchi et al. |

FOREIGN PATENT DOCUMENTS

| | | |
|---|---|---|
| CN | 206865186 U | 1/2018 |
| JP | 2009-240016 A | 10/2009 |
| JP | 2010-093880 A | 4/2010 |
| JP | 2013-150593 A | 8/2013 |
| JP | 2014-512207 A | 5/2014 |
| JP | 2015-500647 A | 1/2015 |
| JP | 2017-503520 A | 2/2017 |
| JP | 2017-513463 A | 6/2017 |
| JP | 2018-504922 A | 2/2018 |
| JP | 2018-174123 A | 11/2018 |
| WO | 2015/078010 A1 | 6/2015 |
| WO | 2017-175218 A2 | 10/2017 |
| WO | 2018-163261 A1 | 9/2018 |

OTHER PUBLICATIONS

Decision to Grant Patent issued in related Japanese Patent Application No. 2019-035984 dated Dec. 17, 2019.
Notice of Reasons for Refusal issued in related Japanese Patent Application No. 2019-035984 dated Jun. 25, 2019.
Notice of Reasons for Refusal issued in related Japanese Patent Application No. 2019-035984 dated Oct. 8, 2019.
Office Action dated Apr. 16, 2021, in Chinese Patent Application No. 202010051372.2.

\* cited by examiner

US 11,031,801 B2

POWER SUPPLY UNIT FOR AEROSOL INHALER

CROSS-REFERENCE TO RELATED APPLICATIONS

This application is based upon and claims the benefit of priority from prior U.S. provisional application No. 62/793,551, filed on Jan. 17, 2019 and prior Japanese patent application No. 2019-035984, filed on Feb. 28, 2019, the entire contents of which are incorporated herein by reference.

TECHNICAL FIELD

The present invention relates to a power supply unit for an aerosol inhaler.

BACKGROUND ART

In Patent Literature 1, a non-combustion type flavor inhaler including an atomizing unit having a load for atomizing an aerosol source without combustion, and a power supply unit including a power supply for supplying power to the load is disclosed. In general, a power supply unit includes not only a power supply but also a connector that can be electrically connected to an external power supply, and a control device (a control unit, a charger, and so on) that is configured to control at least one of charging and discharging of the power supply or that is configured to be able to convert power which is input from the connector into charging power for the power supply.

For example, in Patent Literature 2, a power supply unit having a plurality of capacitors provided on the downstream side from a charger so as to be connected in parallel with the charger is disclosed. In Patent Literature 3, a power supply unit having a capacitor provided between a connector and a charger so as to be connected in parallel with the charger in order to stabilize voltage to be input to the charger is disclosed.

[Patent Literature 1] WO 2018/163261 A1
[Patent Literature 2] CN 206865186 U
[Patent Literature 3] US 2015/0173124 A1

However, even though the capacitors are provided on the downstream side of the charger, it is not possible to stabilize voltage to be input to the charger, and even though the capacitor is provided between the connector and the charger, if high-frequency noise is input, inappropriate voltage may be supplied to the control device.

An object of the present invention is to provide a power supply unit for an aerosol inhaler capable of appropriately protecting a control device.

SUMMARY OF INVENTION

According to an aspect of the invention, there is provided a power supply unit for an aerosol inhaler, the power supply unit comprising: a power supply able to discharge power to a load for generating an aerosol from an aerosol source; a connector able to be electrically connected to an external power supply; and a control device configured to control at least one of charging and discharging of the power supply or configured to be able to convert power which is input from the connector into charging power for the power supply, wherein the power supply unit further includes: a conductor which electrically connects the connector and the control device; a capacitor which is provided between the connector and the control device so as to be connected in parallel with the control device; a first circuit board on which the connector is provided; a second circuit board which is apart from the first circuit board and on which the capacitor and the control device are provided; and a conductive member which electrically connects the first circuit board and the second circuit board.

DESCRIPTION OF EMBODIMENTS

Figure 1:
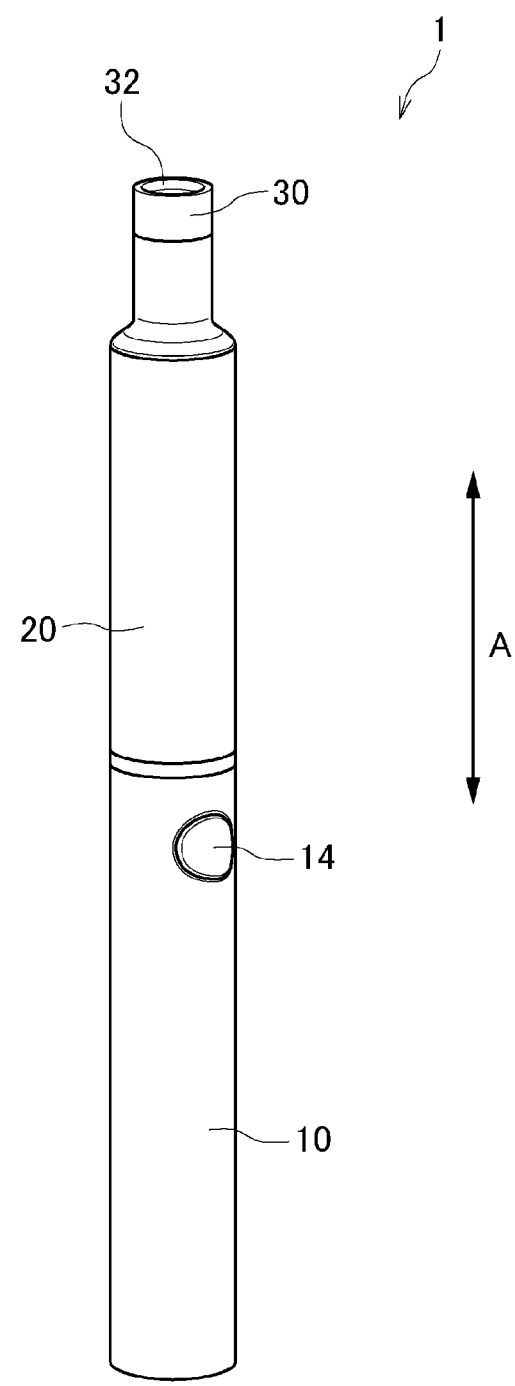
FIG. 1 is a perspective view of an aerosol inhaler equipped with a power supply unit of an embodiment of the present invention.
Figure 2:
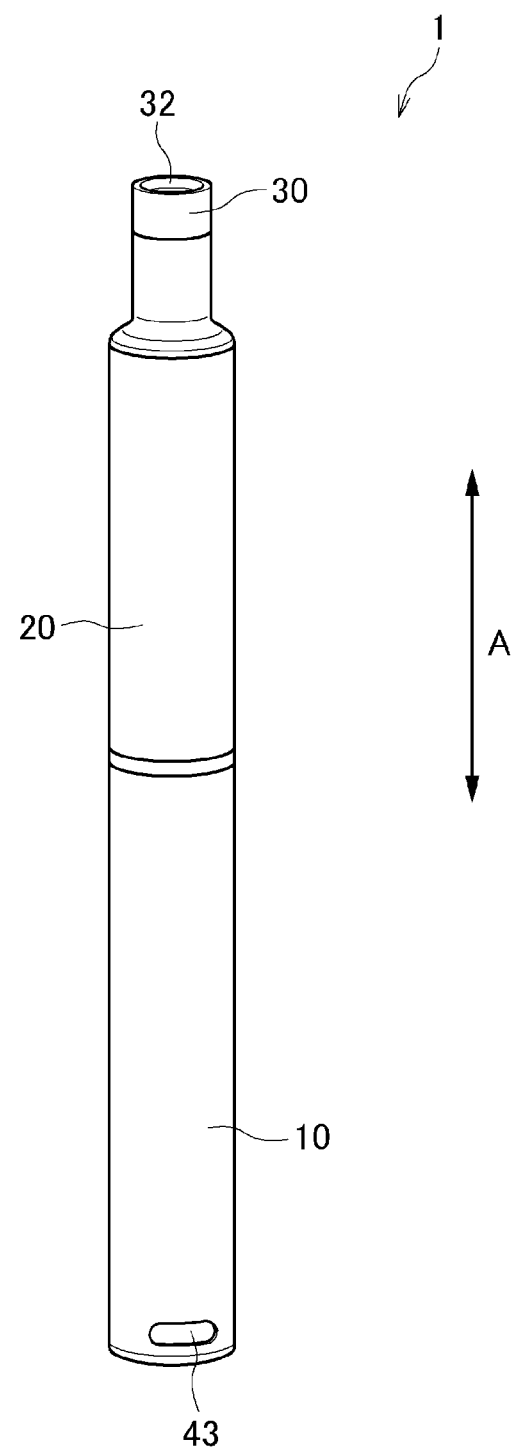
FIG. 2 is another perspective view of the aerosol inhaler of FIG. 1.

Hereinafter, a power supply unit for an aerosol inhaler according to an embodiment of the present invention will be described. First of all, an aerosol inhaler equipped with the power supply unit will be described with reference to FIG. 1 to FIG. 3.

(Aerosol Inhaler)

An aerosol inhaler 1 is a device for inhaling a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10, and the second cartridge 30 can be attached to and detached from the first cartridge 20. In other words, the first cartridge 20 and the second cartridge 30 can be individually replaced.

(Power Supply Unit)

The power supply unit 10 of the present embodiment includes a power supply 12, a charger 13, a control unit 50, various sensors, and so on inside a cylindrical power supply unit case 11, as shown in FIG. 3 to FIG. 6. The power supply 12 is a chargeable secondary battery, an electric double-layer capacitor, or the like, and is preferably a lithium-ion battery.

On a top part 11*a* of the power supply unit case 11 positioned on one end side in the longitudinal direction A (the first cartridge (20) side), a discharging terminal 41 is provided. The discharging terminal 41 is provided so as to protrude from the top surface of the top part 11*a* toward the first cartridge 20, and is configured to be able to be electrically connected to a load 21 of the first cartridge 20.

Further, on a part of the top surface of the top part 11*a* in the vicinity of the discharging terminal 41, an air supply part 42 for supplying air to the load 21 of the first cartridge 20 is provided.

On a bottom part 11*b* of the power supply unit case 11 positioned on the other end side in the longitudinal direction (the opposite side to the first cartridge 20), a charging terminal 43 able to be electrically connected to an external power supply 60 (see FIG. 7) capable of charging the power supply 12 is provided. The charging terminal 43 is provided on the side surface of the bottom part 11*b*, such that at least one of USB terminals, micro USB terminals, and Lightning (registered as a trade mark) terminals can be connected thereto.

However, the charging terminal 43 may be a power receiving part able to receive power from the external power supply 60 in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from the external power supply 60 without any contact point. As another example, the charging terminal 43 may be configured such that at least one of USB terminals, micro USB terminals, and Lightning (registered as a trade mark) terminals can be connected thereto and the above-mentioned power receiving part is included therein.

In other words, the discharging terminal 41 and the charging terminal 43 are separately configured, and are disposed apart from each other in the longitudinal direction A. Therefore, the power supply unit 10 is configured such that in a state where discharging of the power supply 12 through the discharging terminal 41 is possible, it is possible to electrically connect the external power supply 60 to the charging terminal 43. Also, in the power supply unit 10, in a state where the charging terminal 43 and the external power supply 60 are electrically connected, if an aerosol generation request is detected, it is prohibited to perform charging and discharging of the power supply 12 at the same time.

Also, on the side surface of the top part 11*a* of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line L of the power supply unit 10 in the longitudinal direction A. The operation unit 14 is composed of a button type switch, a touch panel, or the like, and is used to activate and shut off the control unit 50 and various sensors and perform other operations according to the intention of a user to use. In the vicinity of the operation unit 14, the control unit 50 and an inhalation sensor 15 for detecting puff actions are provided.

The charger 13 controls charging power to be input from the charging terminal 43 to the power supply 12. The charger 13 is configured with a charging IC including a converter for converting direct current, which is applied from an inverter 61 or the like provided for converting alternating current into direct current on a charging cable which is connected to the charging terminal 43, into direct current having a different magnitude, a voltmeter, an ammeter, a processor, and so on.

Figure 6:
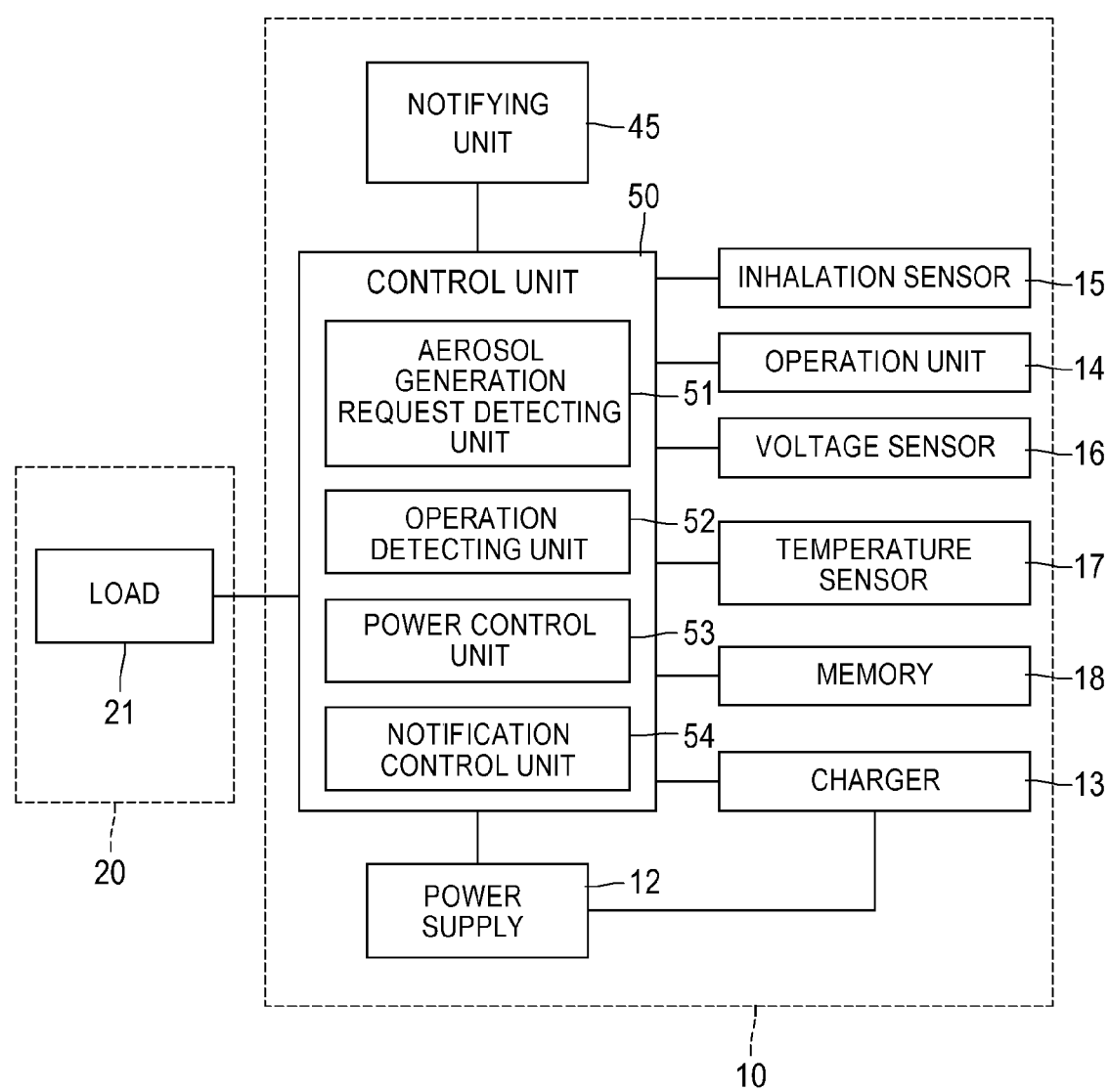
FIG. 6 is a block diagram illustrating the main part configuration of the power supply unit in the aerosol inhaler of FIG. 1.

The control unit 50 is connected to the charger 13, the operation unit 14, various sensor devices such as the inhalation sensor 15 for detecting puff (inhalation) actions, a voltage sensor 16 for measuring the voltage of the power supply 12, and so on, and a memory 18 for storing the number of puff actions, the time for which power has been applied to the load 21, and so on, as shown in FIG. 6, and performs a variety of control on the aerosol inhaler 1. The inhalation sensor 15 may be compose of a capacitor microphone, a pressure sensor, or the like. The control unit 50 is specifically a processor (a micro controller unit (MCU)). The structure of this processor is more specifically an electric circuit configured by combining circuit elements such as semiconductor elements and so on. The details of the control unit 50 will be described below.

Also, in the power supply unit case 11, an air intake (not shown in the drawings) for taking in air is formed. The air intake may be formed around the operation unit 14, or may be formed around the charging terminal 43.

(First Cartridge)

Figure 3:
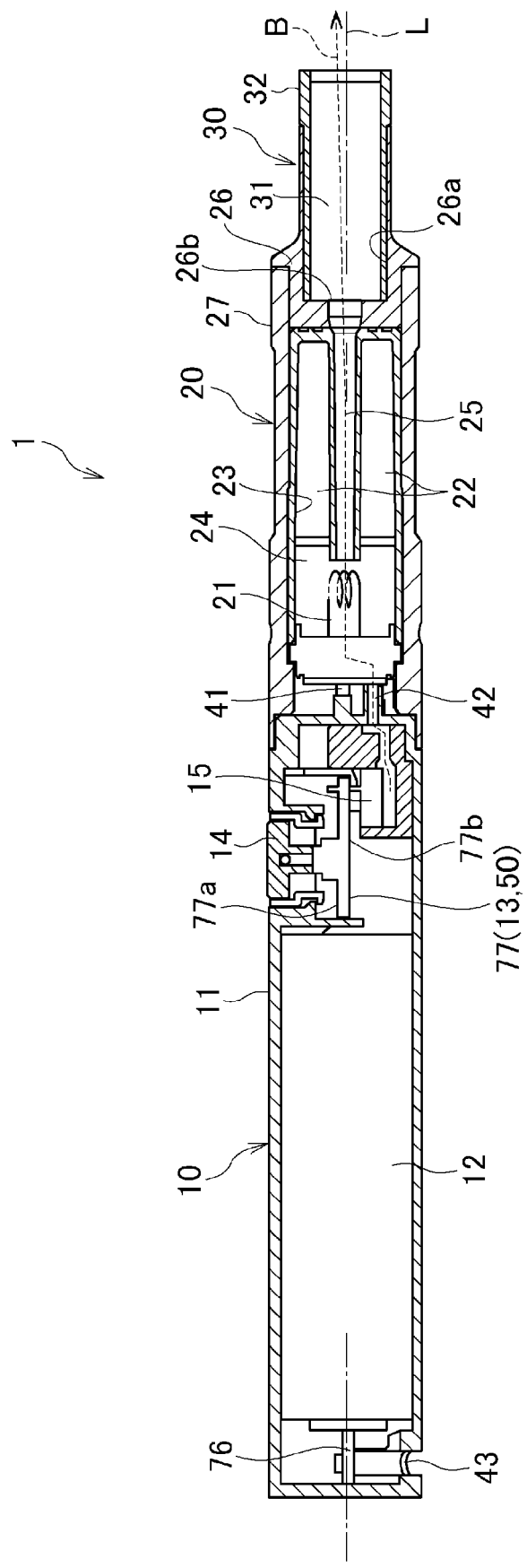
FIG. 3 is a cross-sectional view of the aerosol inhaler of FIG. 1.
Figure 4:
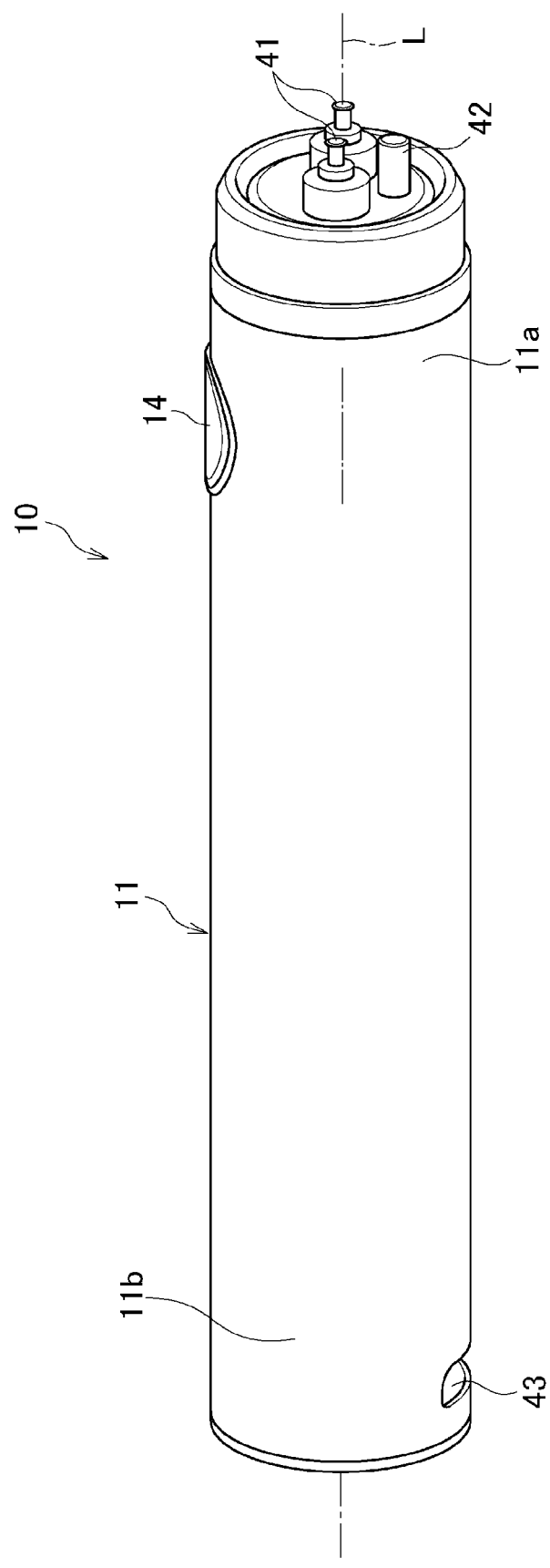
FIG. 4 is a perspective view of the power supply unit in the aerosol inhaler of FIG. 1.

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, and an end cap 26 for storing a part of the second cartridge 30, inside a cylindrical cartridge case 27.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 from the reservoir 23 toward the load 21 using capillarity, and is configured with, for example, glass fiber, a porous ceramic, or the like.

The load 21 atomizes the aerosol source 22, without combustion, by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heat generating element or an ultrasonic wave generator. Examples of the heat generating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26*a* for storing a part of the second cartridge 30, and a connecting passage 26*b* for connecting the aerosol channel 25 and the cartridge storage part 26*a*.

(Second Cartridge)

The second cartridge 30 holds a flavor source 31. An end part of the second cartridge 30 on the first cartridge (20) side is stored in the cartridge storage part 26a provided in the end cap 26 of the first cartridge 20, so as to be able to be removed. Another end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with plants (such as mint, herbal medicines, and herbs) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 can be referred to as an aerosol generation source for generating an aerosol.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, the notifying unit 45 for notifying a variety of information is provided (see FIG. 6). The notifying unit 45 may be configured with a light emitting element, or may be configured with a vibrating element, or may be configured with a sound output element. Alternatively, the notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by light emitting elements such as LEDs to pass through.

(Electric Circuit)

Now, the electric circuit of the power supply unit 10 will be described with reference to FIG. 7.

The power supply unit 10 includes the power supply 12, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the control unit 50 which is connected between the positive electrode side of the power supply 12 and the positive electrode side discharging terminal 41a and between the negative electrode side of the power supply 12 and the negative electrode side discharging terminal 41b, the charger 13 which is disposed on the power transmission path between the charging terminal 43 and the power supply 12, a switch 19 which is disposed on the power transmission path between the power supply 12 and the discharging terminal 41, and a first zener diode 71, a second zener diode 72, a resistor 73, a first capacitor 74, and a second capacitor 75 to be described below. The switch 19 is configured with, for example, a MOSFET, and is turned on and off according to gate voltage which is adjusted by the control unit 50.

(Control Unit)

As shown in FIG. 6, the control unit 50 includes an aerosol generation request detecting unit 51, an operation detecting unit 52, a power control unit 53, and a notification control unit 54.

The aerosol generation request detecting unit 51 detects a request for aerosol generation based on the output result of the inhalation sensor 15. The inhalation sensor 15 is configured to output the value of a variation in the pressure in the power supply unit 10 caused by inhalation of the user through the inhalation port 32. The inhalation sensor 15 is, for example, a pressure sensor for outputting an output value (for example, a voltage value or a current value) according to the atmospheric pressure which varies according to the flow rate of air which is sucked from the intake (not shown in the drawings) toward the inhalation port 32 (i.e. a puff action of the user).

The operation detecting unit 52 detects operations which are performed on the operation unit 14 by the user.

The notification control unit 54 controls the notifying unit 45 such that the notifying unit notifies a variety of information. For example, the notification control unit 54 controls the notifying unit 45 in response to detection of the timing to replace the second cartridge 30, such that the notifying unit notifies the timing to replace the second cartridge 30. The notification control unit 54 notifies the timing to replace the second cartridge 30, based on the number of puff actions or the cumulative time for which power has been supplied to the load 21, stored in the memory 18. The notification control unit 54 is not limited to notification of the timing to replace the second cartridge 30, and may notify the timing to replace the first cartridge 20, the timing to replace the power supply 12, the timing to charge the power supply 12, and so on.

The power control unit 53 controls discharging of the power supply 12 through the discharging terminal 41 by switching on and off the switch 19, if the aerosol generation request detecting unit 51 detects the request for aerosol generation.

The power control unit 53 performs control such that the amount of aerosol which is generated by atomizing the aerosol source by the load 21 falls in a desired range, i.e. such that the amount of power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

After supply of power to the load 21 starts, if a predetermined period passes, the power control unit 53 stops supply of power from the power supply 12 to the load 21. In other words, even while the user is actually performing a puff action, if the puff period exceeds a certain period, the power control unit 53 stops supply of power from the power supply 12 to the load 21. The certain period is determined to suppress variation in user's puff period. The power control unit 53 controls the on/off duty ratio of the switch 19 for one puff action, according to the amount of power stored in the power supply 12. For example, the power control unit 53 controls the interval between ON periods in which power is supplied from the power supply 12 to the load 21 (the pulse interval) and controls the length of each ON period in which power is supplied from the power supply 12 to the load 21 (the pulse width).

Also, the power control unit 53 detects an electric connection between the charging terminal 43 and the external power supply 60, and controls charging of the power supply 12 through the charger 13.

(Board Configuration)

Figure 5:
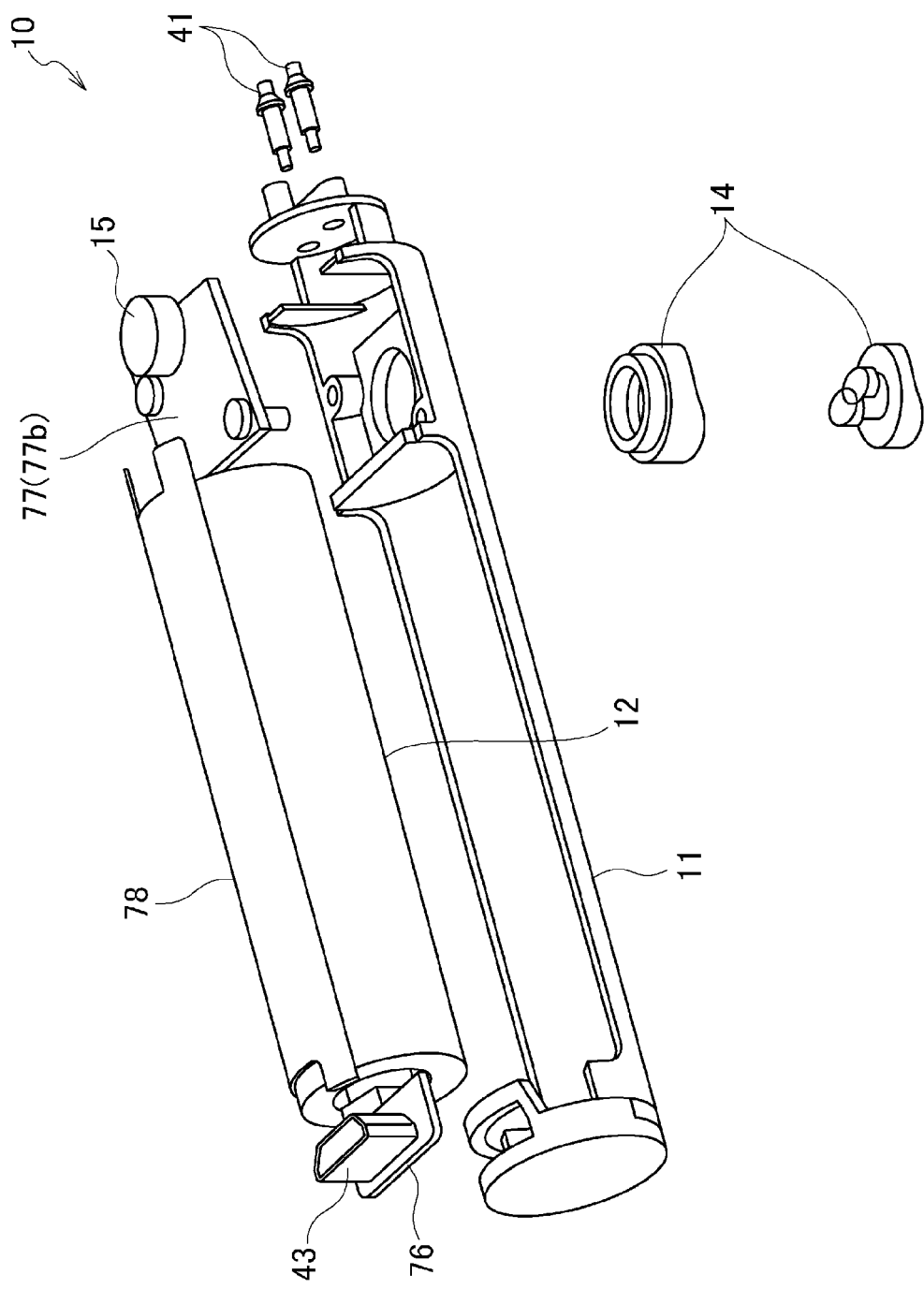
FIG. 5 is an exploded perspective view illustrating the internal configuration of the power supply unit in the aerosol inhaler of FIG. 1.
Figure 7:
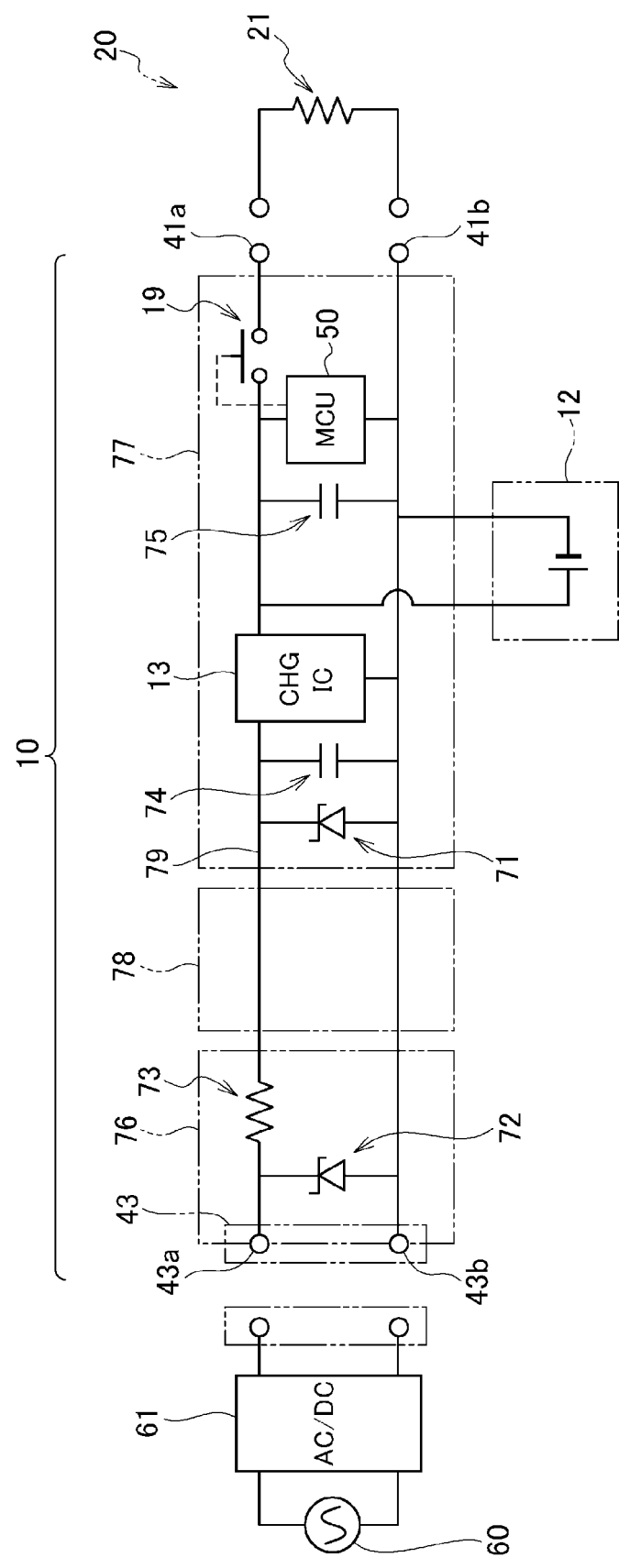
FIG. 7 is a schematic diagram illustrating the circuit configuration of the power supply unit in the aerosol inhaler of FIG. 1.

As shown in FIG. 5 and FIG. 7, the power supply unit 10 includes a first circuit board 76 on which the charging terminal 43, the second zener diode 72, and the resistor 73 are provided, a second circuit board 77 on which the control unit 50, the charger 13, the switch 19, the first zener diode 71, the first capacitor 74, the second capacitor 75, the operation unit 14, and the inhalation sensor 15 are provided, and a conductive member 78 which electrically connects the first circuit board 76 and the second circuit board 77. The conductive member 78 is a part of a conductor which electrically connects the charging terminal 43 and the charger 13, and the conductive member 78 of the present embodiment is configured with a flexible circuit board; however, it may be configured with a conductive wire.

As shown in FIG. 5, the first circuit board 76 and the second circuit board 77 are disposed apart from each other. Specifically, on one end side of the power supply 12 in the longitudinal direction (the longitudinal direction A), the first circuit board 76 is provided, and on the other end side of the power supply 12 in the longitudinal direction (the longitudinal direction A), the second circuit board 77 is provided, and the first circuit board 76 and the second circuit board 77 are electrically connected through the conductive member 78 extending in the longitudinal direction of the power supply 12 along the periphery of the power supply 12. Alternatively, on one end side of the power supply 12 in the width direction (the direction perpendicular to the longitudinal direction A), the first circuit board 76 may be provided, and on the other end side of the power supply 12 in the width direction, the second circuit board 77 may be provided.

(First Zener Diode)

Figure 8A:
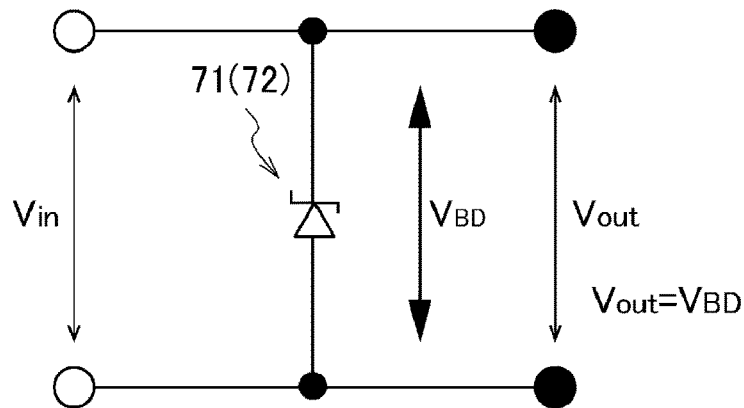
FIG. 8A is a circuit diagram including a zener diode.
Figure 8B:
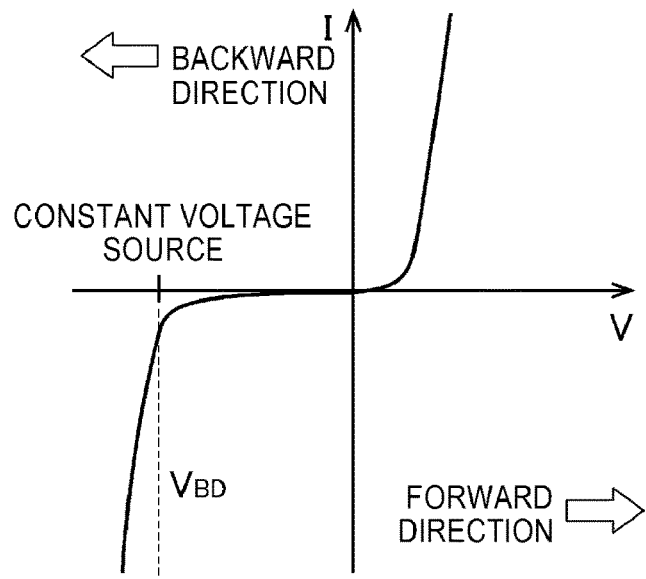
FIG. 8B is an explanatory view illustrating the breakdown voltage of the zener diode.
Figure 8C:
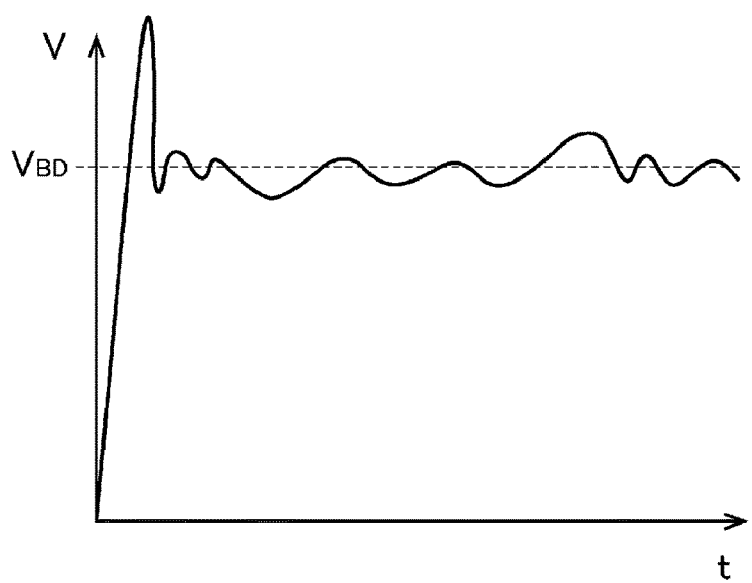
FIG. 8C is an explanatory view illustrating pulsation of input voltage for a charger.
Figure 8D:
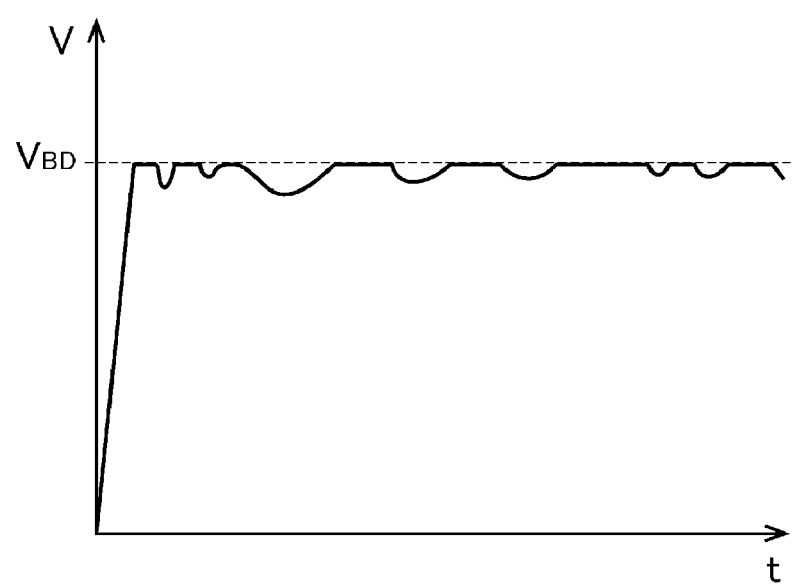
FIG. 8D is an explanatory view illustrating voltage stabilization attributable to the zener diode.

The first zener diode 71 is provided between the charging terminal 43 and the charger 13 so as to be connected in parallel with the charger 13. According to this first zener diode 71, it is possible to stabilize voltage to be input to the charger 13. In other words, as shown in FIG. 8B, the zener diode has a small breakdown voltage $V_{BD}$ at which current flowing in the backward direction suddenly increases (the backward current prevention action which the diode originally has is lost). Therefore, the zener diode is likely to break down. In this case, as shown in FIG. 8A, the voltage between both ends of the zener diode is fixed at $V_{BD}$, and the relation of Vout (Output Voltage)=$V_{BD}$ is established. Therefore, even though input voltage Vin pulsates as shown in FIG. 8C, stable output voltage Vout without pulsation as shown in FIG. 8D is obtained.

Also, in a circuit shown in FIG. 8A, it should be noted that in the case where voltage which is applied between both ends of the zener diode is lower than the breakdown voltage, the output voltage Vout becomes equal to the input voltage Vin.

The first zener diode 71 is connected closer to the input terminal of the charger 13 than to the output terminal of the charging terminal 43. According to this first zener diode 71, in addition to stabilization of voltage which is supplied from the charging terminal 43, it is possible to eliminate pulsation of the voltage attributable to an L (reactance) component ineluctably existing between the charging terminal 43 and the charger 13, thereby appropriately protecting the charger 13. This ineluctably existing L component is caused by, for example, the conductive member 78 and the resistor 73.

As described above, the first zener diode 71 is provided on the second circuit board 77. In other words, since the charging terminal 43 and the charger 13 are provided on the different circuit boards 76 and 77, the degree of freedom in laying out individual components in the power supply unit 10 is high. Also, since the first zener diode 71 is provided on the second circuit board 77 where the charger 13 is provided, it is possible to dispose the first zener diode 71 close to the charger 13. However, the first zener diode 71 may be provided on the downstream side of the conductive member 78 in the flow direction of power which is input from the charging terminal 43, not on the second circuit board 77. Even in this case, it is possible to dispose the first zener diode 71 close to the charger 13. If the first zener diode is disposed close to the charger 13 as described above, it is possible to input voltage stabilized by eliminating pulsation by the first zener diode 71, to the charger 13.

The first zener diode 71 is directly connected to a bus 79 which electrically connects the charging terminal 43 and the charger 13. In other words, since the first zener diode 71 is connected without a switch such as a transistor interposed therebetween, it is possible to avoid an increase in the size of the structure around the first zener diode 71. Furthermore, in the aerosol inhaler 1, since large current and high voltage are not handled, even if the first zener diode 71 is not connected to a switch such as a transistor, it is possible to sufficiently stabilize voltage.

(Second Zener Diode)

The second zener diode 72 is provided between the charging terminal 43 and the first zener diode 71 so as to be connected in parallel with the first zener diode 71. According to this configuration, while fluctuations in voltage which is input from the external power supply are eliminated by the second zener diode 72, pulsation of the voltage attributable to the L component ineluctably existing between the charging terminal 43 and the charger 13 is eliminated by the first zener diode 71. Therefore, it is possible to more surely protect the charger 13. Also, since different roles are assigned to the first zener diode 71 and the second zener diode 72, it is possible to restrain the sizes and costs of the zener diodes from increasing. Furthermore, it is possible to restrain heat generation from being concentrated in one zener diode. Moreover, since the L component responds to change in voltage or current over time, fluctuations in voltage which is input from the external power supply are eliminated by the second zener diode 72 disposed immediately before the place where the L component occurs. Therefore, it is possible to apply stabler voltage to the charger 13.

As described above, the second zener diode 72 is provided on the first circuit board 76, and the first zener diode 71 is provided on the second circuit board 77 apart from the first circuit board 76. However, the second zener diode 72 may be provided on the upstream side of the conductive member 78 in the flow direction of power which is input from the charging terminal 43, and the first zener diode 71 may be provided on the downstream side of the conductive member 78 in the flow direction of power which is input from the charging terminal 43.

The first zener diode 71 and the second zener diode 72 are configured with identical components. In this case, component management becomes easy, and it is possible to reduce the costs of the zener diodes.

(Zener Voltage)

Figure 9:
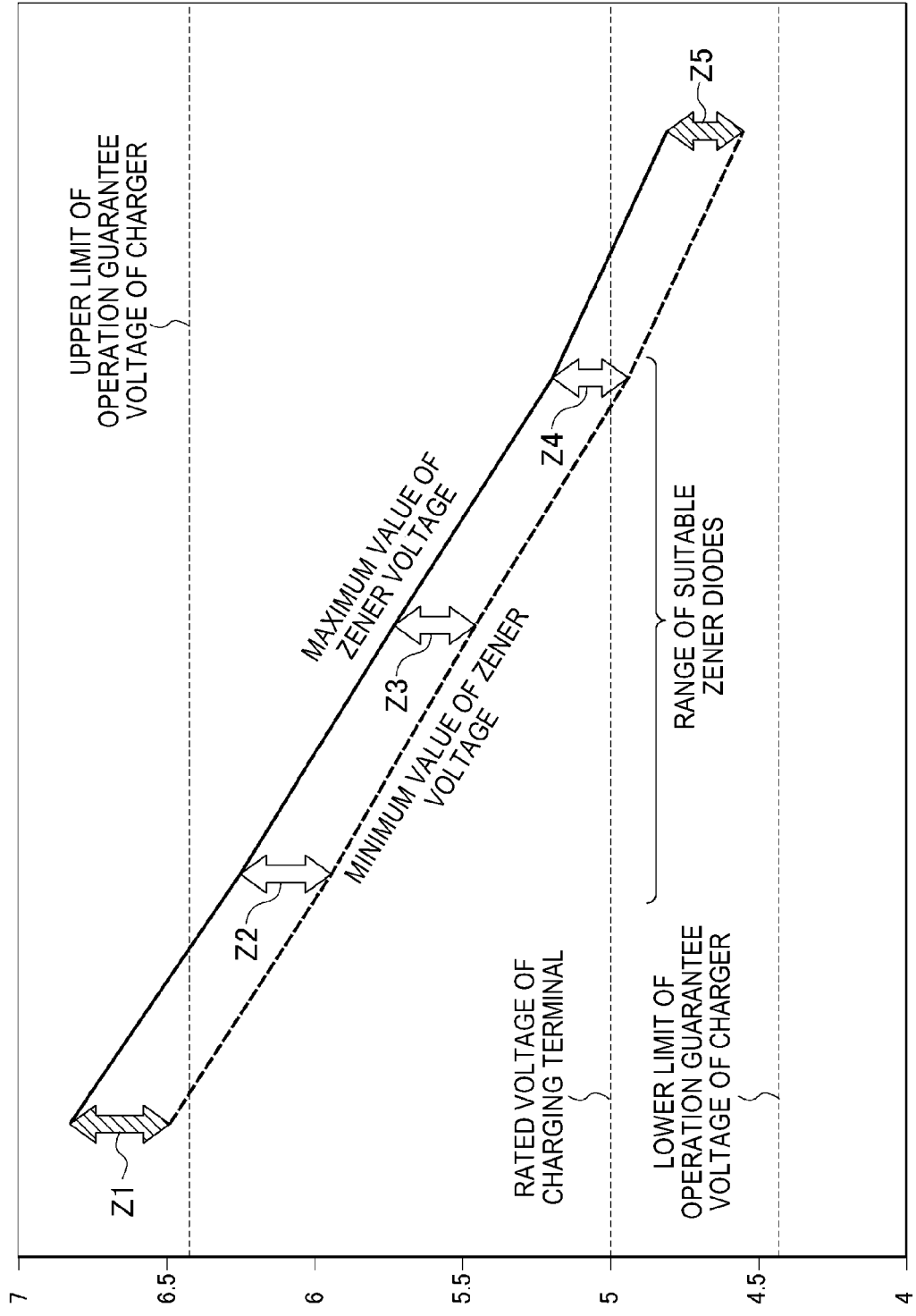
FIG. 9 is an explanatory view illustrating a range of zener diodes suitable as a second zener diode (or a first zener diode) of the power supply unit in the aerosol inhaler of FIG. 1.

Now, a range (a zener voltage range) of zener diodes suitable as the second zener diode 72 and the first zener diode 71 will be described with reference to FIG. 9. The zener voltage of a general zener diode is defined as a range which is defined by a minimum value and a maximum value, not as a certain specific value. In the following description, the second zener diode 72 will be described as an example.

The maximum value of the zener voltage of the second zener diode 72 is lower than the maximum operation guarantee voltage (for example, 6.45 V) of the charger 13. According to this configuration, it is possible to avoid voltage equal to or higher than the maximum operation guarantee voltage from being input to the charger 13, and it is possible to stably input voltage lower than the maximum operation guarantee voltage.

The minimum value of the zener voltage of the second zener diode 72 is higher than the minimum operation guarantee voltage (for example, 4.45 V) of the charger 13.

According to this configuration, is possible to avoid voltage lower than the minimum operation guarantee voltage from being input to the charger 13, and it is possible to stably input voltage equal to or higher than the minimum operation guarantee voltage.

A value which is obtained by subtracting the maximum value of the zener voltage of the second zener diode 72 from the maximum operation guarantee voltage of the charger 13 is smaller than a value which is obtained by subtracting the minimum operation guarantee voltage of the charger 13 from the minimum value of the zener voltage of the second zener diode 72. According to this configuration, it is possible to lower the frequency at which the second zener diode 72 breaks down. Therefore, it is possible to suppress heat generation of the second zener diode 72, and it is possible to extend the life of the second zener diode 72.

Actually, the resistance values of general zener diodes and currents which flow through the zener diodes in the breakdown state are not small. Therefore, it is preferable that heat generation of zener diodes in the breakdown state should be suppressed. Also, in the case where voltage to be input to the charger 13 is lower than the maximum operation guarantee voltage of the charger 13, stabilization of the voltage by the zener diode is not essential.

The rated value of voltage which can be supplied from the charging terminal 43 (for example, 5.0 V) is higher than the minimum operation guarantee voltage of the charger 13, and the minimum value of the zener voltage of the second zener diode 72 is higher than the rated value of voltage which can be supplied from the charging terminal 43 (the rated voltage). According to this configuration, the second zener diode 72 never breaks down. Therefore, it is possible to efficiently use the second zener diode 72 with respect to voltage which is supplied from the charging terminal 43.

A value which is obtained by subtracting the maximum value of the zener voltage of the second zener diode 72 from the maximum operation guarantee voltage of the charger 13 is smaller than a value which is obtained by the rated value of voltage which can be supplied from the charging terminal 43 from the minimum value of the zener voltage of the second zener diode 72. According to this configuration, it is possible to lower the frequency at which the second zener diode 72 breaks down. Therefore, it is possible to suppress heat generation of the second zener diode 72, and it is possible to extend the life of the second zener diode 72.

For each of components (Z1 to Z5 of FIG. 9) for zener diodes, a minimum value for zener voltage and a maximum value for zener voltage are determined. Therefore, a zener diode having the above-mentioned zener voltage range is selected. Therefore, as the second zener diode 72 and the first zener diode 71, the components Z2 to Z4 are preferable, and the component Z2 is most preferable. In the second zener diode 72 and the first zener diode 71, identical components may be used, or different components may be used.

In the above-described embodiment, in order to stabilize voltage to be input to the charger 13, the second zener diode 72 is used. However, in order to stabilize voltage to be input to the control unit 50, another zener diode may be used. Since the control unit 50 also has a maximum operation guarantee voltage and a minimum operation guarantee voltage similarly to the charger 13, it is possible to use zener diodes having appropriate zener voltage ranges based on them.

(Resistor)

The resistor 73 is provided between the first zener diode 71 and the second zener diode 72 so as to be connected in series with the first zener diode 71 and the second zener diode 72. According to this configuration, since voltage is dropped by the resistor 73, it is possible to prevent high voltage from being input to the charger 13. Furthermore, since voltage equal to or higher than the zener voltage is unlikely to be applied to the first zener diode 71, it is possible to suppress heat generation of the first zener diode 71.

The resistor 73 is connected on the upstream side from the conductive member 78 in the flow direction of power which is input from the charging terminal 43. Specifically, the resistor 73 is provided on the first circuit board 76 apart from the second circuit board 77 on which the charger 13 is provided. According to this configuration, it is possible to separate the resistor 73 which is a heat generating element from the charger 13.

(First Capacitor)

The first capacitor 74 is provided between the charging terminal 43 and the charger 13 so as to be connected in parallel with the charger 13. According to this configuration, it is possible to make the first capacitor 74 function as a smoothing capacitor to stabilize voltage to be input to the charger 13. Also, the first capacitor 74 is connected to the conductor so as to be closer to the charger 13 than to the charging terminal 43. Therefore, it is possible to further stabilize voltage to be input to the charger 13.

Since the resistance component of the conductor electrically connecting the charging terminal 43 and the charger 13 and the first capacitor 74 constitute a low pass filter, it is possible to restrain high-frequency noise from being input to the charger 13. Also, since the first capacitor 74 is provided between the first zener diode 71 and the charger 13 so as to be connected in parallel with the charger 13, minor changes in voltage which cannot be eliminated by the first zener diode are smoothed by the first capacitor 74. Therefore, it is possible to input stabler voltage to the charger 13. Also, in the case of using the above-described resistor 73, the resistor 73 also constitutes a part of the low pass filter.

Figure 10:
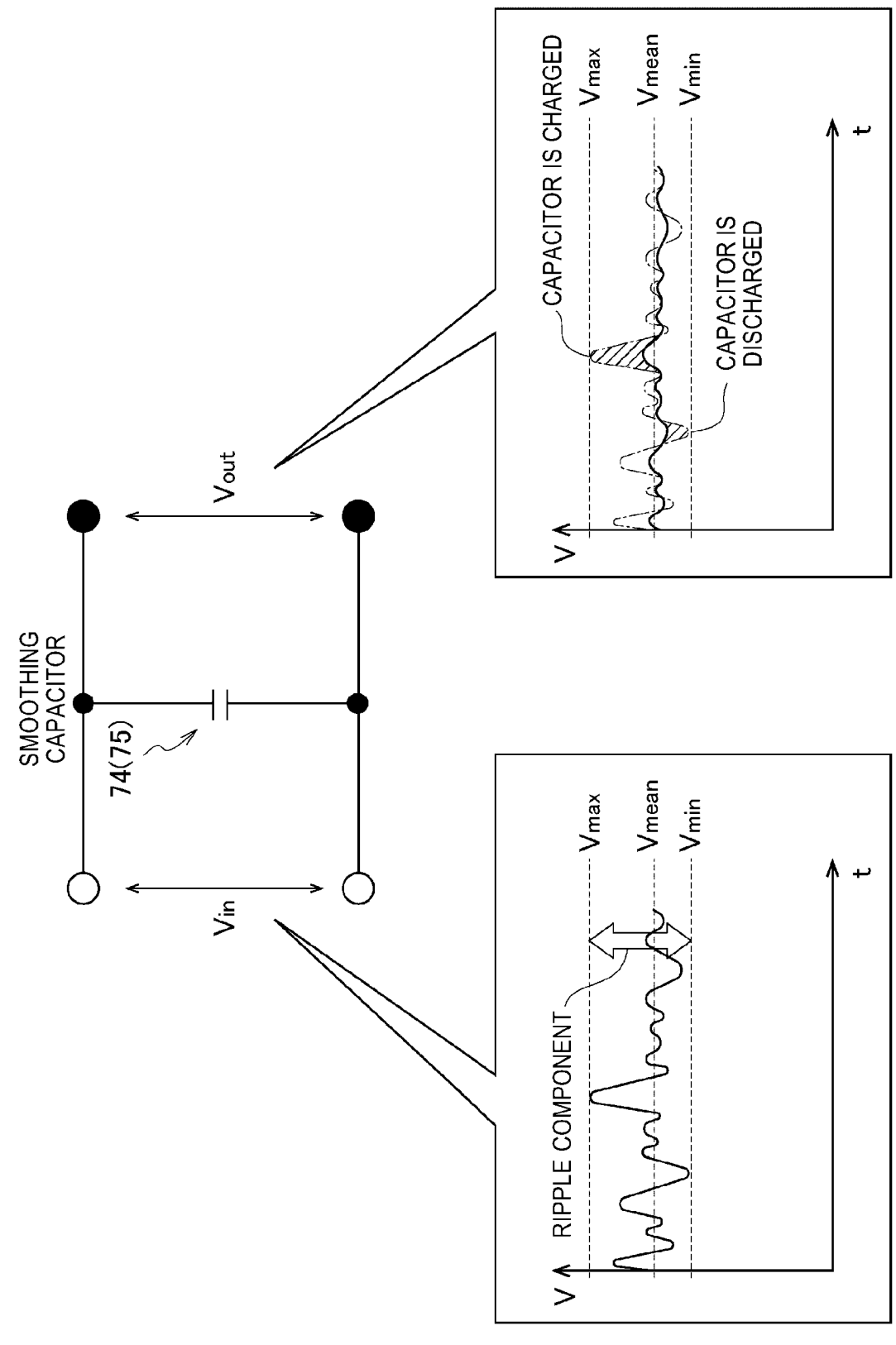
FIG. 10 is an explanatory view illustrating the operation principle of a smoothing capacitor of the power supply unit in the aerosol inhaler of FIG. 1.
Figure 11:
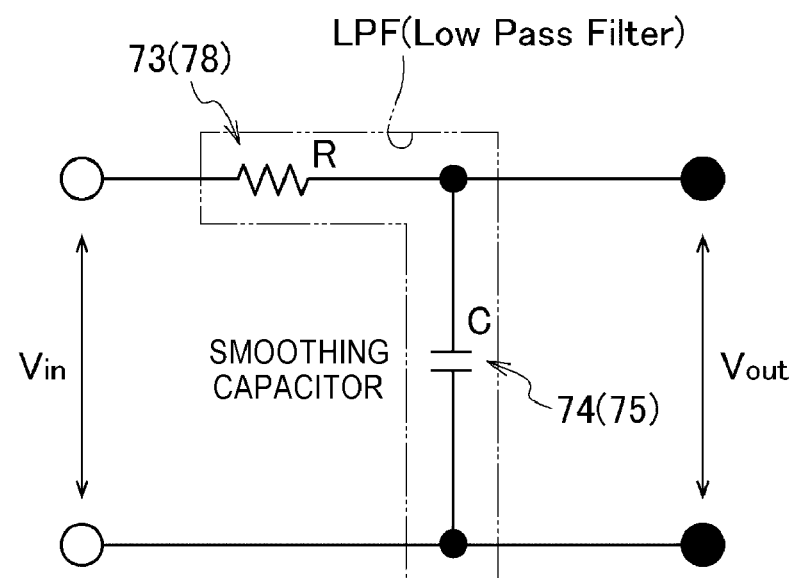
FIG. 11 is a circuit diagram including a low pass filter.

Therefore, as shown in FIG. 10, the smoothing capacitor smoothes ripple components (pulsation components) included in input voltage Vin, using the charging action and discharging action of the capacitor, thereby stabilizing output voltage Vout. Also, the low pass filter is a filter which is composed of a capacitor (C) and a resistance component (R), as shown in FIG. 11, and removes high-frequency noise, and passes low-frequency noise. The cutoff frequency f of the low pass filter (the maximum frequency of frequencies which the low pass filter passes) is expressed as the following formula.

$$f=1/2\pi RC$$

In order to reduce the area on the circuit board which the first capacitor 74 occupies, it is preferable to reduce the capacity (size) of the first capacitor within such a range that the first capacitor can eliminate ripple components. However, if the capacity of the first capacitor 74 is reduced, the cutoff frequency becomes higher. Therefore, there is a possibility that the first cartridge cannot exhibit sufficient noise removal performance. For this reason, in the power supply unit 10 of the present embodiment, while the capacity of the first capacitor 74 is set to be small, the resistance component is set to be large. As a result, the cutoff frequency is suppressed so as to be low, and necessary noise removal performance is secured. Hereinafter, configurations for setting the resistance component to be large will be listed.

As described above, the first capacitor 74 is provided on the second circuit board 77, together with the charger 13. The second circuit board 77 is apart from the first circuit board 76 on which the charging terminal 43 is provided, and is electrically connected to the first circuit board 76 through the conductive member 78. In other words, on the upstream side of the first capacitor 74, the conductive member 78 exists, and the cutoff frequency becomes low due to the resistance component of the conductive member 78. Therefore, it is possible to improve noise removal performance.

As described above, the first circuit board 76 is provided on one end side of the power supply 12 in the longitudinal direction (or the width direction), and the second circuit board 77 is provided on the other end side of the power supply 12 in the longitudinal direction (or the width direction). In other words, the first circuit board 76 and the second circuit board 77 are provided on the opposite sides of the power supply 12 in the longitudinal direction (or the width direction). Therefore, it is possible to secure the length of the conductive member 78. As a result, it is possible to increase the resistance component of the conductive member 78, thereby lowering the cutoff frequency. In other words, it is possible to widen the frequency band of removable noise.

On the input side of the first capacitor 74, i.e. on the conductor between the first capacitor 74 and the charging terminal 43, the above-mentioned resistor 73 is provided. The resistance component of the resistor 73 lowers the cutoff frequency. Therefore, it is possible to improve noise removal performance. Also, since the resistor 73 drops voltage, it is possible to restrain high voltage from being input to the charger 13. Also, since the resistor 73 is provided on the first circuit board 76, it is possible to decrease the amount of heat generation of the second circuit board 77 on which the charger 13 and the control unit 50 are provided.

According to the above-described configuration, the resistance component is set to be large. Therefore, it is possible to suppress the cutoff frequency so as to be low, and secure necessary noise removal performance.

The capacity of the first capacitor 74 can be set to 1 µF or less. According to this configuration, by selecting a capacitor having sufficient capacity required for the power supply unit 10 for the aerosol inhaler, it is possible to avoid the size of the power supply unit 10 from increasing.

Also, it is preferable that the capacity of the first capacitor 74 should be 0.1 µF or less. According to this configuration, it is possible to reduce the size of the power supply unit 10 while selecting a capacitor having sufficient capacity required for the power supply unit 10 for the aerosol inhaler.

(Second Capacitor)

The second capacitor 75 is connected on the input side of the control unit 50, in parallel with the control unit 50. According to this configuration, by making the second capacitor 75 function as a smoothing capacitor, it is possible to stabilize voltage to be input to the control unit 50. Similarly to the first capacitor 74, the second capacitor 75 also is connected to the conductor so as to be closer to the control unit 50 than to the charging terminal 43. Therefore, it is possible to further stabilize voltage to be input to the control unit 50.

The capacity of the second capacitor 75 is different from the capacity of the first capacitor 74. In other words, since objects (the charger 13 and the control unit 50) which the first capacitor 74 and the second capacitor 75 should protect are different, by selecting capacitors having appropriate capacities according to the objects to be protected, it is possible to reduce the areas on the board which the capacitors occupy.

The maximum operation guarantee voltage of the charger 13 (for example, 6.45 V) is higher than the maximum operation guarantee voltage of the control unit 50 (for example, 5.5 V). For this reason, as the second capacitor 75, a capacitor having a capacity larger than that of the first capacitor 74 is selected. As described above, the capacity of the second capacitor 75 which is provided on the input side of the control unit 50 having low withstand voltage performance is set to be larger than the capacity of the first capacitor 74 which is provided on the input side of the charger 13. Therefore, it is possible to more surely protect the control unit 50 inferior in withstand voltage performance.

The charger 13 is configured to be able to control charging of the power supply 12, and operate only during charging of the power supply 12, and the control unit 50 is configured to operate during charging of the power supply 12 and during discharging of the power supply. Therefore, as the second capacitor 75, a capacitor having a capability larger than that of the first capacitor 74 is selected. As described above, the capacity of the second capacitor 75 which is provided on the input side of the control unit 50 which operations during charging of the power supply 12 and during discharging is set to be larger than the capacity of the first capacitor 74 which is provided on the input side of the charger 13 which operates only during charging. Therefore, it is possible to more surely protect the important control unit 50 to be frequently used.

The control cycle (operation clock) of the charger 13 is longer than the control cycle of the control unit 50. For this reason, as the second capacitor 75, a capacitor having a capacity larger than that of the first capacitor 74 is selected. As described above, the capacity of the second capacitor 75 which is provided on the input side of the control unit 50 having the short control cycle is set to be larger than the capacity of the first capacitor 74 which is provided on the input side of the charger 13 having the long control cycle.

Therefore, it is possible to more surely protect the control unit 50 having high performance.

The control unit 50 is electrically connected to the operation unit 14 which the user can operate, and the inhalation sensor 15 for detecting inhaling actions of the user. For this reason, as the second capacitor 75, a capacitor having a capacity larger than that of the first capacitor 74 is selected. According to this configuration, since the capacity of the second capacitor 75 which is provided on the input side of the control unit 50 which is electrically connected to the operation unit 14 and the inhalation sensor 15 is set to be larger than that of the first capacitor 74, it is possible to more surely protect the control unit 50 likely to be influenced by electrostatic noise entering through the operation unit 14 and the inhalation sensor 15.

On the input side of the first capacitor 74, the first zener diode 71 is provided so as to be connected in parallel with the first capacitor 74. Therefore, even if the capacity of the first capacitor 74 is set to be smaller than the capacity of the second capacitor 75, it is possible to protect the charger 13 by the voltage stabilization action of the first zener diode 71.

It is preferable that the capacity of the second capacitor 75 should be 10 times to 100 times the capacity of the first capacitor 74. For example, the capacity of the first capacitor 74 is set to 0.1 µF, and the capacity of the second capacitor 75 is set to 10 µF. As described above, capacitors having appropriate capacities according to objects to be protected are mounted. Therefore, it is possible to reduce the areas on the board which the capacitors occupy while protecting the objects.

(Layout on Second Circuit Board)

As shown in FIG. 3 and FIG. 5, the operation unit 14 and the inhalation sensor 15 are provided on the second circuit board 77. Electrostatic noise such as static electricity entering through the operation unit 14 and the inhalation sensor 15 is smoothed by the capacitors 74 and 75 which are provided on the second circuit board 77.

The second circuit board 77 has a first main surface 77a, and a second main surface 77b which is the back of the first main surface 77a, and the operation unit 14 is provided on the first main surface 77a, and the inhalation sensor 15 is provided on the second main surface 77b. As described above, the operation unit 14 and the inhalation sensor 15 are provided on the different surfaces of the second circuit board 77. Therefore, it is possible to restrain electrostatic noise entering through the operation unit 14 and electrostatic noise entering through the inhalation sensor 15 from being superimposed to form large noise.

The capacitors 74 and 75 are provided on the second main surface 77b of the second circuit board 77. In other words, the second main surface 77b is a circuit mounting surface. As described above, the capacitors 74 and 75 and the operation unit 14 are provided on the different surfaces of the second circuit board 77. Therefore, it is possible to secure a space for the capacitors 74 and 75 to be disposed.

The operation unit 14 is required to be exposed from the surface of the power supply unit 10 because of its role, so it is likely to become an electrostatic noise entry route. Electrostatic noise is received by the first main surface 77a, not directly by the second main surface 77b on which the capacitors 74 and 75 are provided. Therefore, it is possible to restrain electrostatic noise from reaching the second main surface 77b. Therefore, capacitors having large capacities are unnecessary. Therefore, it is possible to reduce the areas on the board which capacitors occupy.

However, the present invention is not limited to the above-described embodiment, and modifications, improvements, etc. can be made properly.

In the configuration shown in the above-described embodiment, in order to protect the charger 13, the first capacitor 74 is configured to function as a smoothing capacitor and a low pass filter with respect to power which is supplied from the charging terminal 43 to the charger 13. However, for example, in order to protect the control unit 50, at least one of the first capacitor 74 and the second capacitor 75 may be configured to function as a smoothing capacitor and a low pass filter with respect to power which is supplied from the charging terminal 43 to the control unit 50.

In this specification, at least the following inventions (1) to (15) are disclosed. Moreover, although the corresponding constituent elements and the like in the embodiments described above are shown in parentheses, it is not limited thereto.

(1) A power supply unit (the power supply unit 10) for an aerosol inhaler (the aerosol inhaler 1), the power supply unit comprising:

a power supply (the power supply 12) able to discharge power to a load (the load 21) for generating an aerosol from an aerosol source (the aerosol source 22);

a connector (the charging terminal 43) able to be electrically connected to an external power supply (the external power supply 60); and a control device (the control unit 50 and the charger 13) configured to control at least one of charging and discharging of the power supply or configured to be able to convert power which is input from the connector into charging power for the power supply, wherein the power supply unit further includes:

a conductor which electrically connects the connector and the control device;

a capacitor (the first capacitor 74 or the second capacitor 75) which is provided between the connector and the control device so as to be connected in parallel with the control device;

a first circuit board (the first circuit board 76) on which the connector is provided;

a second circuit board (the second circuit board 77) which is apart from the first circuit board and on which the capacitor and the control device are provided; and a conductive member (the conductive member 78) which electrically connects the first circuit board and the second circuit board.

According to (1), since the power supply unit includes the capacitor which is provided between the connector and the control device so as to be connected in parallel with the control device, it is possible to stabilize voltage to be input to the control device. Also, since the resistance component of the conductor and the capacitor constitute a low pass filter, it is possible to restrain high-frequency noise from being input to the control device.

Furthermore, since the connector and the control device are provided on the different circuit boards, the degree of freedom in laying out the individual components in the power supply unit is high. Moreover, since the cutoff frequency is lowered by the resistance component of the conductive member, noise removal performance improves.

(2) A power supply unit (the power supply unit 10) for an aerosol inhaler (the aerosol inhaler 1), the power supply unit comprising:
- a power supply (the power supply 12) able to discharge power to a load (the load 21) for generating an aerosol from an aerosol source (the aerosol source 22);
- a connector (the charging terminal 43) able to be electrically connected to an external power supply (the external power supply 60); and
- a control device (the control unit 50 and the charger 13) configured to control at least one of charging and discharging of the power supply or configured to be able to convert power which is input from the connector into charging power for the power supply, wherein the power supply unit further includes:
  - a conductor (the conductive member 78) which electrically connects the connector and the control device; and
  - a capacitor (the first capacitor 74 or the second capacitor 75) which is connected in parallel with the control device and which is connected to the conductor so as to be closer to the control device than to the connector.

According to (2), since the power supply unit includes the capacitor which is connected in parallel with the control device and is connected to the conductor so as to be closer to the control device than to the connector, it is possible to stabilize voltage to be input to the control device. Furthermore, since the resistance component of the conductor and the capacitor constitute a low pass filter, it is possible to restrain high-frequency noise from being input to the control device.

(3) The power supply unit according to (2), wherein the power supply unit further includes:
- a first circuit board (the first circuit board 76) on which the connector is provided;
- a second circuit board (the second circuit board 77) which is apart from the first circuit board and on which the capacitor and the control device is provided; and
- a conductive member (the conductive member 78) that electrically connects the first circuit board and the second circuit board.

According to (3), since the connector and the control device are provided on the different circuit boards, the degree of freedom in layout is high. Moreover, since the cutoff frequency is lowered by the resistance component of the conductive member, noise removal performance improves.

(4) The power supply unit according to (1) or (3), wherein the first circuit board is provided on one end side of the power supply in a longitudinal direction, and the second circuit board is provided on the other end side in the longitudinal direction.

According to (4), since the first circuit board and the second circuit board are provided on the opposite sides of the power supply in the longitudinal direction, it is possible to secure the length of the conductive member. Therefore, it is possible to increase the resistance component of the conductive member.

(5) The power supply unit according to (1) or (3), wherein the first circuit board is provided on one end side of the power supply in a width direction, and the second circuit board is provided on the other end side in the width direction.

According to (5), since the first circuit board and the second circuit board are provided on the opposite sides of the power supply in the width direction, it is possible to secure the length of the conductive member. Therefore, it is possible to increase the resistance component of the conductive member.

(6) The power supply unit according to any one of (1), and (3) to (5), wherein
the power supply unit further includes at least one of a switch (the operation unit 14) which a user can operate and a sensor (the inhalation sensor 15) which is configured to output an inhaling action of a user, and
the switch or the sensor is provided on the second circuit board.

According to (6), since the switch or the sensor is provided on the second circuit board, it also is possible to smooth electrostatic noise such as static electricity entering through the switch or the senor, by the capacitor.

(7) The power supply unit according to any one of (1), and (3) to (6), wherein
the power supply unit further includes:
- a switch (the operation unit 14) which a user can operate; and
- a sensor (the inhalation sensor 15) configured to output an inhaling action of the user, and
the switch and the sensor are provided on the second circuit board.

According to (7), since the switch and the sensor are provided on the second circuit board, it also is possible to smooth electrostatic noise such as static electricity entering through the switch and the senor, by the capacitor.

(8) The power supply unit according to (7), wherein
the second circuit board has a first main surface (the first main surface 77a), and a second main surface (the second main surface 77b) which is a back of the first main surface,
the switch is provided on the first main surface, and the sensor is provided on the second main surface.

According to (8), since the switch and the senor are provided on the different surfaces of the second circuit board, it is possible to restrain electrostatic noise entering through the switch and electrostatic noise entering through the sensor from being superimposed to form large noise.

(9) The power supply unit according to (8), wherein
the capacitor is provided on the second main surface.

According to (9), since the capacitor and the switch are provided on the different surfaces of the board, it is possible to secure a space for the capacitor to be disposed. Moreover, it is possible to separate the capacitor from the switch which is likely to become an electrostatic noise entry route since it needs to be exposed to the outside. Therefore, it is possible to restrain electrostatic noise from reaching the surface having the capacitor provided thereon.

(10) The power supply unit according to any one of (1), and (3) to (9), wherein
the power supply unit further includes a resistor (the resistor 73) which is connected in series between the connector and a connection point between the conductor and an input side of the capacitor.

According to (10), since the resistor is provided immediately before the capacitor, the cutoff frequency is lowered by the resistance component of the resistor. Therefore, the noise removal performance improves. Moreover, since the resistor drops voltage, it is possible to restrain high voltage from being input to the control device.

(11) The power supply unit according to (10), wherein
the resistor is provided on the first circuit board.

According to (11), since the resistor is provided on the first circuit board, as compared to the case of providing the resistor on the second circuit board on which the control device is provided, it is possible to reduce the amount of heat generation of the second circuit board.

(12) The power supply unit according to (1) to (11), wherein
a capacity of the capacitor is 1 µF or less.

According to (12), by selecting a capacitor having a sufficient capacity required for the power supply unit for the aerosol inhaler, it is possible to avoid the size of the power supply unit from increasing.

(13) The power supply unit for an aerosol inhaler according to (1) to (12), wherein
a capacity of the capacitor is 0.1 µF or less.

According to (13), by selecting a capacitor having a sufficient capacity required for the power supply unit for the aerosol inhaler, it is possible to avoid the size of the power supply unit from increasing.

(14) A power supply unit (the power supply unit 10) for an aerosol inhaler (the aerosol inhaler 1), the power supply unit comprising:
  a power supply (the power supply 12) able to discharge power to a load (the load 21) for generating an aerosol from an aerosol source (the aerosol source 22);
  a connector (the charging terminal 43) able to be electrically connected to an external power supply (the external power supply 60); and
  a control device (the control unit 50 and the charger 13) configured to control at least one of charging and discharging of the power supply or configured to be able to convert power which is input from the connector into charging power for the power supply, wherein
  the power supply unit further includes a capacitor (the first capacitor 74 or the second capacitor 75) which is provided between the connector and the control device so as to be connected in parallel with the control device, and
  the capacitor is configured to function as a smoothing capacitor and a low pass filter with respect to power which is supplied from the connector to the control device.

According to (14), since the capacitor which is provided between the connector and the control device so as to be connected in parallel with the control device is configured to function as a smoothing capacitor and a low pass filter with respect to power which is supplied from the connector to the control device, it is possible to stabilize voltage to be input to the control device. Therefore, it is possible to restrain high-frequency noise from being input to the control device.

(15) The power supply unit according to (14), wherein
the power supply unit further includes a resistor (the resistor 73) which is connected in series between the connector and a connection point between an input side of the capacitor and a conductor (the conductive member 78) which electrically connects the connector and the control device.

According to (15), since the resistor is provided immediately before the capacitor, the cutoff frequency is lowered by the resistance component of the resistor. Therefore, the noise removal performance improves. Moreover, since the resistor drops voltage, it is possible to restrain high voltage from being input to the control device.

What is claimed is:
1. A power supply unit for an aerosol inhaler, the power supply unit comprising:
  a lithium-ion secondary battery which is a power supply able to discharge a power to a load for generating an aerosol from an aerosol source;
  a connector able to be electrically connected to an external power supply;
  a charger configured to be able to convert a power which is input from the connector into a charging power for the power supply; and
  a control unit which is configured to control discharging of the power supply to the load and which is a separate component from the charger, wherein
  the power supply unit further includes:
  a conductor which electrically connects the connector and the charger and which is configured to supply the power which is input from the connector to the charger;
  a smoothing capacitor which is provided between the connector and the charger so as to be connected in parallel with the charger;
  a first circuit board on which the connector is provided;
  a second circuit board which is apart from the first circuit board and on which the smoothing capacitor and the charger are provided; and
  a conductive member which electrically connects the first circuit board and the second circuit board.

2. The power supply unit according to claim 1, wherein
the first circuit board is provided on one end side of the power supply in a longitudinal direction, and
the second circuit board is provided on another end side of the power supply in the longitudinal direction.

3. The power supply unit according to claim 1, wherein
the first circuit board is provided on one end side of the power supply in a width direction, and
the second circuit board is provided on another end side of the power supply in the width direction.

4. The power supply unit according to claim 1, wherein
the power supply unit further includes at least one of a switch which can be activated to operate by a user and a sensor which is configured to output an inhaling action of the user, and
the switch or the sensor is provided on the second circuit board.

5. The power supply unit according to claim 1, wherein
the power supply unit further includes:
  a switch which can be activated to operate by a user; and
  a sensor configured to output an inhaling action of the user, and
the switch and the sensor are provided on the second circuit board.

6. The power supply unit according to claim 5, wherein
the second circuit board has a first main surface, and a second main surface which is a back of the first main surface,
the switch is provided on the first main surface, and
the sensor is provided on the second main surface.

7. The power supply unit according to claim 6, wherein
the smoothing capacitor is provided on the second main surface.

8. The power supply unit according to claim 1, wherein
the power supply unit further includes a resistor which is connected in series between the connector and a connection point between the conductor and an input side of the smoothing capacitor.

9. The power supply unit according to claim 8, wherein
the resistor is provided on the first circuit board.

10. The power supply unit according to claim 1, wherein
a capacity of the smoothing capacitor is 1 µF or less.

11. The power supply unit according to claim 1, wherein
a capacity of the smoothing capacitor is 0.1 µF or less.

12. The power supply unit according to claim 1, wherein the smoothing capacitor is connected on a power transmission path between the power supply and the connector without a switch.

* * * * *